United States Patent [19]

Witte et al.

[11] 4,443,477

[45] Apr. 17, 1984

[54] SULPHONAMIDOPHENYLCARBOXYLIC ACID COMPOUNDS AND PHARMACEUTICAL COMPOSITIONS CONTAINING THEM

[75] Inventors: Ernst-Christian Witte, Mannheim; Hans P. Wolfe, Hirschberg-Grossachsen; Karlheinz Stegmeier, Heppenheim; Egon Roesch, Mannheim, all of Fed. Rep. of Germany

[73] Assignee: Boehringer Mannheim GmbH, Mannheim, Fed. Rep. of Germany

[21] Appl. No.: 395,882

[22] Filed: Jul. 7, 1982

Related U.S. Application Data

[63] Continuation of Ser. No. 215,469, Dec. 11, 1980, abandoned.

[30] Foreign Application Priority Data

Jan. 7, 1980 [DE] Fed. Rep. of Germany ....... 3000377

[51] Int. Cl.³ .................... C07C 143/78; A61K 31/18
[52] U.S. Cl. .................................. 424/319; 424/250; 424/309; 424/310; 424/321; 544/390; 544/391; 560/10; 560/12; 560/13; 562/427; 562/430; 564/88; 564/89; 564/91; 564/99
[58] Field of Search ............................. 560/10, 12, 13; 562/427, 430; 564/84, 88, 89, 91, 99; 424/310, 424/307, 309, 319, 321, 250; 544/390, 391

[56] References Cited

U.S. PATENT DOCUMENTS

| | | | |
|---|---|---|---|
| 2,908,648 | 10/1959 | Spivack | 562/430 |
| 3,027,405 | 3/1962 | Spivack | 562/430 |
| 3,991,106 | 11/1976 | Cragoe | 562/430 |
| 4,112,236 | 9/1978 | Bicking | 560/12 |
| 4,258,058 | 3/1981 | Witte | 560/12 |

*Primary Examiner*—Michael L. Shippen
*Attorney, Agent, or Firm*—Felfe & Lynch

[57] ABSTRACT

The invention provides sulphonamides of the formula

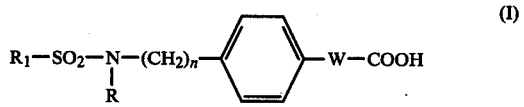

(I)

wherein
R is a hydrogen atom or a lower alkyl radical;
$R_1$ is alkyl, aryl, aralkyl or aralkenyl, the aryl moiety of which in each case can be optionally substituted one or more times by hydroxyl, halogen, trifluoromethyl, lower alkyl or alkoxy or by acyl, carboxy or alkoxycarbonyl;
n is 1, 2 or 3; and
W is a valence bond or a divalent aliphatic hydrocarbon linkage and the physiologically acceptable salts, esters and amides of such compound. These compounds have excellent pharmacological lipid depressing activity and inhibit thrombocyte aggregation.

33 Claims, No Drawings

SULPHONAMIDOPHENYLCARBOXYLIC ACID COMPOUNDS AND PHARMACEUTICAL COMPOSITIONS CONTAINING THEM

This is a continuation application U.S. Ser. No. 215,469 filed Dec. 11, 1980, now abandoned.

This invention relates to new sulphonamidophenylcarboxylic acid compounds, pharmaceutical compositions, for lipid depression and thrombocyte aggregation inhibition, containing such compounds, and to methods for treating infirmities caused by excess lipids or thrombocyte aggregation.

West German Pat. Nos. 26 04 560 and 25 32 420 describe phenylcarboxylic acids substituted by a carbonamide group which have blood sugar-sinking and lipid-sinking activities. It has now surprisingly been found that analogous phenylcarboxylic acids substituted by a sulphonamide group not only exhibit an excellent lipid-sinking action, but also a pronounced inhibition action on thrombocyte aggregation.

Therefore, the present invention provides new sulphonamides of the formula (I):

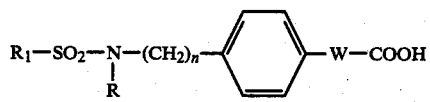
(I)

wherein

R is a hydrogen atom or a lower alkyl radical;

$R_1$ is an alkyl radical or an aryl, aralkyl or aralkenyl radical, the aryl moiety of which in each case can be optionally substituted one or more times by hydroxyl, halogen, trifluoromethyl, lower alkyl or alkoxy or by acyl, carboxy or alkoxycarbonyl;

n is 1, 2 or 3; and

W is a bond or an unbranched or branched divalent aliphatic hydrocarbon chain, which is either saturated or contains a double bond, as well as the physiologically acceptable salts, esters and amides thereof.

The alkyl radical $R_1$ is to be understood to be a straight-chained or branched radical containing up to 16 carbon atoms, preferred examples including the methyl, ethyl, octyl and hexadecyl radicals.

"Lower alkyl" and "lower alkoxy" radicals are, in all cases, to be understood to be straight-chained or branched radicals containing up to 5 carbon atoms. The straight-chained lower alkyl radical is preferably a methyl radical, the branched lower alkyl radical is preferably a tert.-butyl radical and the lower alkoxy radical is preferably a methoxy radical. The acetyl radical is the preferred acyl radical.

The aralkyl radicals are those in which the alkyl moiety contains up to 5 carbon atoms and is straight-chained or branched, the phenethyl and 4-chlorophenethyl radicals being preferred.

The aralkenyl radicals are those in which the alkenyl moiety contains 2 or 3 carbon atoms, the styryl and 4-chlorostyryl radicals being preferred.

The "aryl radical" is to be understood to be an aromatic hydrocarbon radical containing 6 to 14 carbon atoms, the phenyl, biphenylyl, naphthyl and fluorenyl radicals being preferred. These aryl radicals may, in all possible cases, be substituted one or more times, the possible substituents being halogen, alkyl, alkoxy, hydroxyl, trifluoromethyl, carboxyl and acyl.

The halogen atoms are to be understood to be fluorine, chlorine and bromine.

The divalent aliphatic hydrocarbon chain W can contain up to 6 but preferably up to 4 carbon atoms.

When W represents an unbranched chain, it may be one of the following: —CH$_2$—, —(CH$_2$)$_2$— or —(CH$_2$)$_3$— (saturated), or —CH=CH— (unsaturated).

When W represents a branched chain, it may be one of the following:

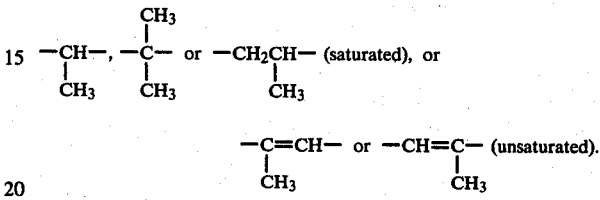

The esters derived from the carboxylic acids of general formula (I) contain, as alcohol component, lower monohydroxy alcohols, of which methanol, ethanol and n-butanol are preferred, or polyhydroxy alcohols, for example glycol or glycerol, or alcohols with other functional groups, for example ethanolamine or glycol ethers.

The amides according to the present invention derived from the carboxylic acids of general formula (I) contain, as amine component, for example, ammonia, p-aminobenzoic acid, β-alanine, ethanolamine or 2-aminopropanol, those previously mentioned being preferred. However, alkylamines, for example isopropylamine or tert.-butylamine, dialkylamines, for example diethylamine, as well as cyclic amines, for example morpholine or 4-alkyl-, 4-aralkyl- or 4-arylpiperazines, such as 4-methylpiperazine, 4-(4-chlorobenzyl)-piperazine or 4-(3-methoxyphenyl)-piperazine can also be used.

The above definitions of the compounds according to the present invention are to be understood to include all possible stereoisomers, as well as mixtures thereof.

The present invention also provides processes for the preparation of sulphonamides of general formula (I), in which R, $R_1$, n and W have the above-given meanings, wherein, for example:

(a) an amine of the general formula:

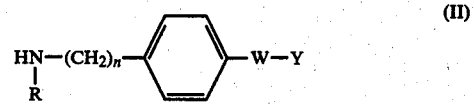
(II)

in which R, n and W have the same meanings as above and Y is a —COOR$_2$ group, R$_2$ being a hydrogen atom or a lower alkyl radical or an acid amide group or a residue which, after condensation has taken place, is converted into a COOR$_2$ group or into an acid amide group, is reacted in per se known manner with a sulphonic acid of the general formula:

$R_1$—SO$_2$OH      (III)

in which $R_1$ has the same meaning as above, or a derivative thereof; or, as a variant of this process, a transacylation is carried out by reacting a free sulphonic acid (III) with a compound of the general formula:

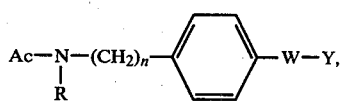
(IV)

in which R, W, Y and n have the same meanings as above and Ac is a readily exchangeable acyl radical in an appropriate solvent; or (b) a sulphonamide of the general formula:

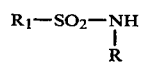
(V)

in which R and $R_1$ have the same meanings as above, is reacted with a compound of the general formula:

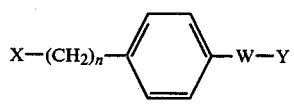
(VI)

in which W, Y and n have the same meanings as above and X is a reactive group; whereafter, if desired, compounds of general formula (I) in which R is a hydrogen atom are alkylated in known manner on the sulphonamide nitrogen atom, acid derivatives obtained of general formula (I) are, if desired, converted into the free acids or, if desired, free acids obtained of the general formula (I) are converted into esters, amides or physiologically acceptable salts; or (c) a compound of the general formula:

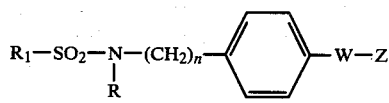
(VII)

in which R, $R_1$, W and n have the same meanings as above and Z is a residue which can be converted by oxidation into a carboxyl group is oxidized.

Further processes for the preparation of the compounds (I) according to the present invention include the following:

(d) a compound of the general formula:

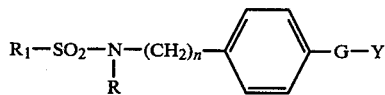
(VIII)

in which R, $R_1$, Y and n have the same meanings as above and G represents a divalent hydrocarbon chain which contains one of the groups

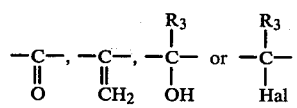

in which $R_3$ is an aliphatic hydrocarbon radical, or a functional derivative of one of these groups is reduced; or, when W represents an unbranched chain, (e) a compound of the general formula:

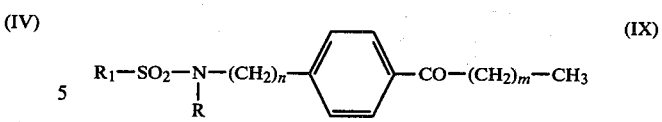
(IX)

in which R, $R_1$ and n have the same meanings as above and m is 0, 1 or 2, is reacted under the conditions of a possibly modified Willgerodt-Kindler reaction.

(f) For the preparation of compounds of the general formula:

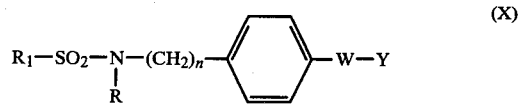
(X)

in which R, $R_1$, Y and n have the same meanings as above and W has the special meaning of

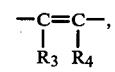

in which $R_3$ and $R_4$, which can be the same or different, are aliphatic hydrocarbon radicals, use can be made of all conventional processes known for the preparation of cinnamic acids and derivatives thereof:

(f 1) In the case of the availability of suitable compounds X, but in which W has the meaning:

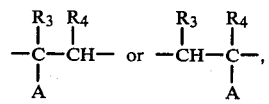

in which $R_3$ and $R_4$ have the same meanings as above and A represents a halogen atom, a hydroxyl group or a functionally changed hydroxyl group, the desired compounds X, in which W represents the radical:

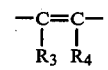

in which $R_3$ and $R_4$ have the same meanings as above, may be obtained by the action of an agent splitting off HA.

(f 2) In the case of the availability of compounds of the general formula:

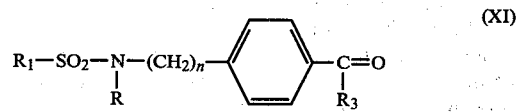
(XI)

in which R, $R_1$, $R_3$ and n have the same meanings as above, the desired cinnamic acid derivatives can be prepared by an aldol condensation type of reaction, i.e. by a reaction with activated CH groups. Examples of such compounds include acetic acid and its derivatives but especially malonic acid derivatives of the general formula:

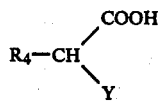

$$\text{(XII)}$$

in which $R_4$ and Y have the same meanings as above, whereby, in the latter case, after condensation has taken place, a decarboxylation occurs.

As further possibility of such aldol-like reactions is the Perkin reaction, in which compounds of the general formula (XI) are reacted with an anhydride of an aliphatic carboxylic acid in the presence of an alkali metal salt, possibly of the same aliphatic carboxylic acid.

(f 3) A third possibility is the reaction of compounds of general formula (XI) with appropriate organophosphorus compounds by means of modified Wittig reactions. Examples of such organophosphorus reaction components include alkoxy-carbonylmethyl-phosphonic acid alkyl esters of the general formula:

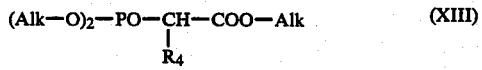

in which $R_4$ has the same meaning as above and Alk is an alkyl radical.

(g) Hydrogenation of the cinnamic acid derivatives obtained according to the above methods f 1 to f 3 or according to other methods gives the analogous compounds with saturated hydrocarbon chains.

Preferred reactive derivatives of the sulphonic acids (III) include the halides and the esters. The reactions of the sulphonic acid halides with compounds of the general formula (II) are preferably carried out with the addition of an acid-binding agent, for example an alkali metal acetate, sodium hydrogen carbonate, sodium carbonate, sodium phosphate, calcium oxide, calcium carbonate or magnesium carbonate. However, organic bases, for example pyridine or triethylamine, can also perform this function, whereby, as inert solvent, there can be used, for example, diethyl ether, benzene, methylene chloride, dioxan or an excess of the tertiary amine.

When using inorganic acid binders, the reaction medium used can be, for example, water, aqueous ethanol or aqueous dioxan.

The transacylation reaction between a free sulphonic acid (III) and an acylamine (IV) is preferably carried out with the use of equimolar amounts of both reaction components in a polar solvent, the polar solvent being, for example, an alcohol, especially ethanol or methanol. The reaction is preferably carried out at the boiling temperature of the solvent. The easily exchangeable acyl radical can be, for example, the acetyl radical.

For the alkylation of the sulphonamides (V), it is preferable to use compounds (VI), in which X is an arylsulphonyloxy radical. Thus, preferred alkylation agents include arylsuphonic acid alkyl esters, a method, the use of which for sulphonic acid amides, has been described, for example, by Klamann et al., Monatshefte fur Chemie, 83, 871/1952. The reaction is carried out in an alkaline medium, a preferred reaction medium being a hot, concentrated aqueous solution of sodium carbonate.

The oxidizable group which can be converted into a carboxyl function is preferably a hydroxymethyl, aminomethyl or formyl group but possibly also an acetyl radical or a functional derivative of one of these groups.

The oxidation can be carried out with conventional oxidation agents, for example manganese-IV compounds, permanganates and dichromates and, in the case of the formyl group, also with atmospheric oxygen or silver oxide and in the case of the acetyl radical, on the other hand, for example with a hypobromite.

Numerous processes can be used for the reduction of the groups G in compounds of general formula (VIII). The reduction of a —CO— group can, for example, be carried out by a Clemmensen reaction, using zinc/hydrochloric acid. However, reduction with hydrogen at atmospheric pressure or at an elevated pressure in the presence of a metal catalyst, for example palladium or platinum, in a solvent, for example acetic acid or a lower alcohol, is preferred.

The groups

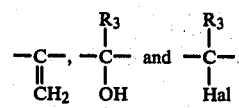

are also preferably reduced by catalytically-activated hydrogen but, when the group G contains a hydroxyl group, reduction is best carried out in the presence of a strong acid, the presence of sulphuric acid or perchloric acid in catalytic amounts being preferred. It is also possible to carry out the reduction with complex metal hydrides, sodium borohydride being preferred. In this case, the reaction can be carried out in an alcohol, especially in methanol, or in dioxan or in an aqueous alkaline medium.

The ketones of general formula (IX) used in the case of process (e) can easily be prepared by a Friedel-Crafts acylation. They are reacted with sulphur and a secondary amine, preferably with morpholine. The thiomorpholide obtained by this Willgerodt-Kindler reaction is saponified in per se known manner with strong alkali lyes or with concentrated hydrochloric acid or with a mixture of sulphuric acid, glacial acetic acid and water, to give the carboxylic acid.

For the preparation of cinnamic acid derivatives according to process (f 1), all processes can be used which split off of HA. If A represents a hydroxyl group, then dehydration can be carried out with conventional agents, for example glacial acetic acid, acetic anhydride, sulphuric acid, hydrogen sulphates, polyphosphoric acid, phosphorus oxychloride, thionyl chloride or phosphorus pentoxide, preferably in the presence of an inert solvent, for example benzene, methylene chloride, carbon tetrachloride or the like, dehydration with phosphorus pentoxide in boiling methylene chloride being preferred. The hydroxy compounds required for the dehydration can be prepared, for example, by a Reformatzky reaction from the corresponding aldehydes or ketones, or they can be obtained by reducing the corresponding keto compounds either with a complex hydride, for example sodium borohydride, or by hydrogenation using a Raney nickel catalyst.

For splitting off a hydrogen halide (when A is a halogen atom), use can be made of basic agents, for example, inorganic or organic bases, such as sodium hydroxide, potassium hydroxide, sodium acetate, sodium carbonate or potassium carbonate, as well as alcoholates, such as sodium methylate, and amines, such as triethylamine, dimethylaniline and pyridine. It is preferable to operate in an inert solvent, for example dioxan, dimethyl sulphoxide, benzene, petroleum ether or an alcohol, such as ethanol or isopropanol.

The condensation of compounds of general formula (XI) with malonic acid derivatives is carried out in known manner by reacting the two reaction components in an appropriate solvent, for example pyridine, preferably in the presence of a primary or secondary amine, piperidine being preferred as the secondary amine.

The reaction between compounds (XI) and phosphonic acid esters (PO-activated olefin compounds according to Horner's method) is carried out in an inert solvent in the presence of a base. The inert solvent can be, for example, diglyme, benzene, toluene, tetrahydrofuran or dimethylformamide but also an ether or petroleum ether. Examples of bases which can be used include sodamide, organolithium compounds, alcoholates (usually dissolved in the corresponding alcohol) and sodium hydride, as well as dimethylsulphoxylate in dimethyl sulphoxide. The reaction may be carried out either at ambient temperature or at an elevated temperature (boiling temperature of the solvent).

The possible subsequent N-alkylation of a compound of general formula (I), in which R is a hydrogen atom, can be carried out by known methods, preferably by reacting a compound in which R is a hydrogen atom with an alkyl halide or a dialkyl sulphate in the presence of an acid-binding agent, for example sodium hydroxide.

Examples of preferred substituents Y in compounds of general formula (IV) include the nitrile, carbaldehyde, hydroxymethyl, aminomethyl and formyl groups.

The conversion of a substituent $R_2$ possibly to be carried out subsequently to the condensation can take place, for example, by saponifying the carboxylic acid esters ($R_2$=alkyl) to the corresponding carboxylic acids ($R_2$=hydrogen) with mineral acids or alkali metal hydroxides in a polar solvent, for example water, methanol, ethanol, dioxan or acetone. The saponification is advantageously carried out with a strong base, such as sodium or potassium hydroxide, in a mixture of methanol and water at ambient temperature or at a moderately elevated temperature. On the other hand, however, the carboxylic acids can be esterified in the usual way or esters with a particular radical $R_2$ can be transesterified to give esters with a different radical $R_2$. The esterification of the carboxylic acids is preferably carried out in the presence of an acid catalyst, for example hydrogen chloride, sulphuric acid or p-toluenesulphonic acid, or of a strongly acidic ion exchange resin. Transesterifications, on the other hand, require the addition of a small amount of a basic substance, for example of an alkali metal and alkaline earth metal hydroxide or of an alkali metal alcoholate. For the esterification of the carboxyl group or for the transesterification, use may, in principle, by made of all alcohols, the lower monohydroxy alcohols being preferred, for example, methanol, ethanol or propanol, as well as the polyhydroxy alcohols, for example, glycol, or alcohols with other functional groups, for example ethanolamine or glycol ethers.

The amides according to the present invention derived from the carboxylic acids of the general formula (I) are preferably prepared by per se known methods from the carboxylic acids or their reactive derivatives, for example, carboxylic acid halides, esters, azides, anhydrides or mixed anhydrides, by reaction with amines. The amino components may be, for example, ammonia, alkylamines and dialkylamines, as well as aminoalcohols, for example, ethanolamine and 2-aminopropanol, and also amino acids, for example p-aminobenzoic acid, β-alanine and the like. Other valuable amino components include the alkyl-, aralkyl- and arylpiperazines.

For the preparation of salts with pharmacologically acceptable organic or inorganic bases, for example sodium hydroxide, potassium hydroxide, calcium hydroxide, ammonium hydroxide, methylglucamine, morpholine or ethanolamine, the carboxylic acids may be reacted with the appropriate bases. Mixtures of the carboxylic acids with an appropriate alkali metal carbonate or hydrogen carbonate can also be considered.

The new compounds of general formula (I) and the physiologically acceptable salts thereof, as well as the esters and amides thereof, show not only an excellent lipid-sinking action but also a marked inhibiting action upon thrombocyte aggregation.

For the preparation of pharmaceutical compositions, the compounds of general formula (I) are mixed in per se known manner with appropriate pharmaceutical carriers and aroma, flavoring and coloring materials and formed, for example, into tablets or dragees or, with the addition of appropriate adjuvants, suspended in water or an oil, for example olive oil.

The compounds of the general formula (I) can be administered orally and parenterally in liquid or solid form. As injection medium, water is preferably used which contains the stabilizing agents, solubilizing agents and/or buffers usual for injection solutions. Examples of such additives include tartrate and borate buffers, ethanol, dimethylsulphoxide, complex formers (such as ethylenediamine-tetraacetic acid), high molecular weight polymers (such as liquid polyethylene oxide) for viscosity regulation and polyethylene derivatives of sorbitol anhydrides.

Examples of solid carrier materials which may be used include starch, lactose, mannitol, methyl cellulose, talc, highly dispersed silicic acid, high molecular weight fatty acids (such as stearic acid), gelatine, agar-agar, calcium phosphate, magnesium stearate, animal and vegetable fats and solid high molecular weight polymers (such as polyethylene glycols). Compositions suitable for oral administration can, if desired, contain flavoring and sweetening materials.

The administered dosage depends upon the age, the state of health and the weight of the recipient, the extent of the disease, the nature of possibly simultaneously carried out further treatments, the frequency of the treatments and the nature of the desired action. The daily dosage of the active compound is usually 0.1 to 50 mg./kg. of body weight. Normally, 0.5 to 40 and preferably 1.0 to 20 mg./kg./day are effective, in one or more applications per day, in order to obtain the desired results.

The superior action of the new compounds according to the present invention in comparison with acetylsalicylic acid is demonstrated by the following experimental results:

Experimental protocol

1. Lipid sinking action

Groups of 10 male and metabolically healthy rats were given the test substance orally for 7 days at a dosage of 50 mg./kg. body weight in the form of a methyl cellulose suspension. At the end of the experimental period and 3 hours after the last administration, the cholesterol and triglyceride values in the serum were determined. The changes were determined in comparison with controls.

2. Aggregation inhibition

The influencing of the thrombocyte aggregation was determined by the Born test:

(a) Methodology

Venous blood from metabolically healthy subjects was mixed with sodium citrate (9:1). The erythrocytes were sedimented by centrifuging at 150 g, the thrombocytes being enriched in the supernatant. This supernatant is called platelet-riched plasma (PRP).

An aliquot of the PRP was introduced into the cuvette of an aggregometer (Universal Aggregometer of the firm Braun, Melsungen) and there stirred with a small magnetic stirrer. The test substance was added in aqueous solution (pH about 7). Changes in the light transmission in the suspension were continuously recorded. After the expiry of the spontaneous aggregation, aggregation was initiated by the addition of $5 \times 10^{-6}$ m adrenalin. Comparatively large thrombocyte aggregates formed and consequently the light transmission through the suspension increased.

(b) Evaluation

The adrenalin-induced aggregation takes place in two stages, i.e. initially the light transmission increases, then briefly stagnates and subsequently again increases. Only the second phase of the aggregation can be influenced by aggregation inhibitors.

For the documentation of the results, the angle of the second aggregation phase to the horizontal for the adrenalin-induced aggregation is determined and taken as being 0% inhibition (control experiment).

Using the same PRP, after the addition of the test substance, aggregation is induced with adrenalin and the course of the aggregation is recorded. The angle of the second phase to the horizontal is again determined and the ratio of the two angles gives the percentage inhibition of the second phase of the thrombocyte aggregation.

In the case of the comparison substance acetylsalicylic acid, the inhibition at a concentration of $10^{-4}$ m is 100% and at a concentration of $5 \times 10^{-5}$ m is 0%. All the substances were tested for aggregation inhibition at a concentration of $5 \times 10^{-5}$ m.

The following Table gives the results obtained in the above-described tests:

TABLE

| Compound of Example No. | Lipid sinking | | Inhibition of adrenalin-induced aggregation |
|---|---|---|---|
| | triglycerides | cholesterol | |
| 1 | 24 | 7 | 0 |
| 1a | 9 | 13 | 100 |
| 1b | 0 | 10 | 0 |
| 1c | 38 | 7 | 100 |
| 1d | 10 | 10 | 0 |
| 3 | 34 | 8 | 100 |
| 3a | 0 | 20 | 0 |
| 3b | 10 | 3 | 0 |
| 3c | 30 | 7 | 50 |
| 3f | 24 | 5 | 100 |
| 3g | 20 | 10 | 30 |
| 4 | 10 | 10 | 100 |
| 4a | 31 | 11 | 100 |
| 4b, 10 | 39 | 16 | 20 |
| 4c | 0 | 12 | 0 |

TABLE-continued

| Compound of Example No. | Lipid sinking | | Inhibition of adrenalin-induced aggregation |
|---|---|---|---|
| | triglycerides | cholesterol | |
| 4d, 9 | 42 | 19 | 100 |
| 4e | 20 | 6 | 100 |
| 4f | 14 | 0 | 100 |
| 4g | 10 | 0 | 100 |
| 4h | 22 | 0 | 50 |
| 4i | 27 | 0 | 100 |
| 4j | 10 | 0 | 10 |
| 4k | 50 | 25 | 50 |
| 4l | 20 | 0 | 100 |
| 4m | 22 | 12 | 100 |
| 5 | 20 | 0 | |
| 6 | 10 | 0 | 0 |
| 7 | 10 | 0 | 0 |

Preferred compounds according to the present invention are, in addition to those described in the specific Examples and to the compounds derived by combination of all of the substituents referred to in the claims, the following:

4-(2-benzenesulphonamidoethyl)-phenylacetamide

3-{4-[2-(4-phenylsulphonamido)-ethyl]-phenyl}-propionic acid

3-{4-[2-(4-phenylsulphonamido)-ethyl]-phenyl}-propionamide and ethyl 3-{4-[2-(4-phenylsulphonamido)-ethyl]-phenyl}-propionate.

The following Examples, which are given for the purpose of illustrating the present invention, illustrate some of the numerous process variants which can be used for the synthesis of the new compounds according to the present invention but without limiting the subject matter of the present invention:

EXAMPLE 1

4-[2-(2-Phenylethanesulphonamido)-ethyl]-benzoic acid

To an ice-cooled solution of 14.3 g. (70 mmol) 4-(2-aminoethyl)-benzoic acid ethyl ester hydrochloride in 150 ml. anhydrous pyridine are added dropwise, in the course of one hour, with stirring, 16.1 g. (70 mmol) 2-phenylethanesulphochloride. The cooling bath is removed and stirring is continued for 2 hours at ambient temperature. Subsequently, the reaction mixture is poured into ice water and acidified with concentrated hydrochloric acid, whereby an oil separates out which is taken up in diethyl ether. The aqueous phase is extracted several times with diethyl ether and the combined etheral phases are dried with anhydrous sodium sulphate and subsequently evaporated. The residue is recrystallized from a mixture of ethyl acetate and ligroin, there being obtained 18.4 g. (73% of theory) ethyl 4-[2-(2-phenylethanesulphonamido)-ethyl]-benzoate; m.p. 83°–86° C.

A mixture of 12.5 g. (35 mmol) ethyl 4-[2-(2-phenylethanesulphonamido)-ethyl]-benzoate, 70 ml. 1 N aqueous potassium hydroxide solution and 200 ml. methanol is kept for 2 hours at 35° C. and then acidified with 2 N hydrochloric acid. The methanol is evaporated off and the remaining aqueous phase is extracted several times with methylene chloride. The combined methylene chloride phases are washed with water, dried over anhydrous sodium sulphate and evaporated. The evaporation residue is dissolved in aqueous sodium hydrogen carbonate solution and precipitated out by the addition of 5 N hydrochloric acid. The crystals obtained are filtered off with suction and dried to give 9.3 g. (88% of theory) 4-[2-(2-phenylethanesulphonamido)-ethyl]-benzoic acid; m.p. 183°–186° C.

The following compounds are obtained in an analogous manner:

(a) ethyl 4-[2-(4-chlorobenzenesulphonamido)-ethyl]-benzoate from ethyl 4-(2-aminoethyl)-benzoate hydrochloride and 4-chlorobenzenesulphochloride; m.p. 87°–89° C.; yield 84% of theory,
and therefrom by hydrolysis
4-[2-(4-chlorobenzenesulphonamido)-ethyl]-benzoic acid; m.p. 199°–201° C.; yield 91% of theory.

(b) ethyl 4-{2-[2-(4-chlorophenyl)-ethanesulphonamido]-ethyl}-phenylacetate from ethyl 4-(2-aminoethyl)-phenylacetate hydrochloride and 2-(4-chlorophenyl)-ethanesulphochloride; m.p. 69°–70° C. (recrystallized from aqueous ethanol); yield 76% of theory,
and therefrom by hydrolysis
4-{2-[2-(4-chlorophenyl)-ethanesulphonamido]-ethyl}-phenylacetic acid; m.p. 155°–156° C. (recrystallized from aqueous ethanol); yield 67% of theory.

(c) ethyl 4-{2-[2-(4-chlorophenyl)-ethenesulphonamido]-ethyl}-phenylacetate from ethyl 4-(2-aminoethyl)-phenylacetate hydrochloride and 2-(4-chlorophenyl)-ethenesulphochloride; m.p. 101°–102° C. (recrystallized from 66% ethanol); yield 70% of theory,
and therefrom by hydrolysis
4-{2-[2-(4-chlorophenyl)-ethenesulphonamido]-ethyl}-phenylacetic acid; m.p. 175°–176° C. (recrystallized from aqueous ethanol); yield 87% of theory.

(d) ethyl 4-[2-(4-chlorobenzenesulphonamido)-ethyl]-phenylacetate
from ethyl 4-(2-aminoethyl)-phenylacetate hydrochloride and 4 chlorobenzenesulphochloride; m.p. 88°–90° C. (recrystallized from ethyl acetate+ligroin); yield 96% of theory,
and therefrom by hydrolysis
4-[2-(4-chlorobenzenesulphonamido)-ethyl]-phenylacetic acid; m.p. 138°–140° C. (recrystallized from ethyl acetate+ligroin); yield 93% of theory.

(e) ethyl 4-[2-(4-carboxybenzenesulphonamido)-ethyl]-phenylacetate
from ethyl 4-(2-aminoethyl)-phenylacetate hydrochloride and 4-carboxybenzenesulphochloride; m.p. (sodium salt) >360° C.; yield 94% of theory,
and therefrom by hydrolysis
4-[2-(4-carboxybenzenesulphonamido)-ethyl]-phenyl acetic acid; m.p. (potassium salt) 340° C.; yield 85% of theory.

EXAMPLE 2

4-(2-Methanesulphonamidoethyl)-benzoic acid 10.6 g. (92 mmol) Methanesulphochloride are introduced dropwise at 10° to 15° C. into a mixture of 150 ml. anhydrous pyridine, 12.8 g. (92 mmol) pulverised, anhydrous potassium carbonate and 21.25 g. (92 mmol) ethyl 4-(2-aminoethyl)-benzoate hydrochloride. Subsequently, the reaction mixture is stirred for 30 minutes at 20° C., then for 5 minutes at 80° C. and thereafter cooled and poured into ice water. It is then acidified with concentrated hydrochloric acid and the precipitate is extracted with methylene chloride. After drying over anhydrous sodium sulphate, the methylene chloride phase is evaporated to give 24.8 g. (98% of theory) ethyl 4-(2-methanesulphonamidoethyl)-benzoate; m.p. 96°–99° C.

By hydrolysis of the ethyl ester analogously to Example 1, there is obtained 4-(2-methanesulphonamidoethyl)-benzoic acid in a yield of 93% of theory; m.p. 173°–174° C.

The following compounds are obtained in an analogous manner:

(a) ethyl 4-(2-methanesulphonamidoethyl)-phenylacetate from ethyl 4-(2-aminoethyl)-phenylacetate hydrochloride and methanesulphochloride; colorless oil; yield 81% of theory,
and therefrom by hydrolysis
4-(2-methanesulphonamidoethyl)-phenylacetic acid; m.p. 170°–172° C. (recrystallized from ethyl acetate+ethanol); yield 79% of theory.

(b) ethyl 2-{4-[2-(2-phenylethanesulphonamido)-ethyl]-phenyl}-propionate
from ethyl 2-[4-(2-aminoethyl)-phenyl]-propionate hydrochloride and 2-phenylethanesulphochloride; colorless oil; yield 77% of theory, and therefrom by hydrolysis
2-{4-[2-(2-phenylethanesulphonamido)-ethyl]-phenyl}-propionic acid; m.p. 94°–97° C. (recrystallized from diethyl ether+ligroin); yield 69% of theory.

(c) ethyl 2-{4-[2-(2-phenylethanesulphonamido)-ethyl]-phenyl}-2-methylpropionate
from ethyl 2-[4-(2-aminoethyl)-phenyl]-2-methylpropionate hydrochloride and 2-phenylethanesulphochloride; colorless oil; yield 52% of theory, and therefrom by hydrolysis
2-{4-[2-(2-phenylethanesulphonamido)-ethyl]-phenyl}-2-methylpropionate; m.p. 109°–110° C. (recrystallized from ethanol+water); yield 62% of theory.

(d) ethyl 3-<4-{2-[2-(4-chlorophenyl)-ethanesulphonamido]-ethyl}-phenyl>-propionate
from ethyl 3-[4-(2-aminoethyl)-phenyl]-propionate hydrochloride and 2-(4-chlorophenyl)-ethanesulphochloride; m.p. 70°–71° C. (recrystallized from ethanol); yield 66% of theory, and therefrom by hydrolysis
3-<4-{2-[2-(4-chlorophenyl)-ethanesulphonamido]-ethyl}-phenyl>-propionic acid; m.p. 157°–158° C. (recrystallized from ethanol+water); yield 76% of theory.

(e) ethyl 3-{4-[2-(4-chlorobenzenesulphonamido)-ethyl]-phenyl}-propionate
from ethyl 3-[4-(2-aminoethyl)-phenyl]-propionate hydrochloride and 4-chlorobenzenesulphochloride; m.p. 61°–62° C. (recrystallized from ethanol); yield 65% of theory,
and therefrom by hydrolysis
3-{4-[2-(4-chlorobenzenesulphonamido)-ethyl]-phenyl}-propionic acid; m.p. 129°–130° C. (recrystallized from ethanol+water); yield 87% of theory.

(f) ethyl 4-[2-(n-hexadecylsulphonamido)-ethyl]-cinnamate from ethyl 4-(2-aminoethyl)-cinnamate hydrochloride and n-hexadecanesulphochloride; m.p. 104° ·C. (recrystallized from ethanol); yield 71% of theory,
and therefrom by hydrolysis
4-[2-(n-hexadecylsulphonamido)-ethyl]-cinnamic acid; m.p. 164°–165° C. (recrystallized from ethanol+water); yield: 76% of theory.

(g) ethyl 4-[2-(2-phenylethanesulphonamido)-ethyl]-cinnamate
from ethyl 4-(2-aminoethyl)-cinnamate hydrochloride and 2-phenylethanesulphochloride; m.p. 98°–99° C.; yield 77% of theory,
and therefrom by hydrolysis
4-[2-(2-phenylethanesulphonamido)-ethyl]-cinnamic acid; m.p. 187°–188° C.; yield 76% of theory.

(h) ethyl 4-{2-[2-(4-chlorophenyl)-ethanesulphonamido]-ethyl}-cinnamate
from ethyl 4-(2-aminoethyl)-cinnamate hydrochloride and 2-(4-chlorophenyl)-ethanesulphochloride; m.p. 91°–92° C. (recrystallized from ethanol+water); yield 63% of theory, and therefrom by hydrolysis 4-{2-[2-(4-chlorophenyl)-ethanesulphonamido]-ethyl}-cinnamic acid; m.p. 212°–213° C. (recrystallized from ethanol+water); yield 94% of theory.

(i) ethyl 4-[2-(4-chlorobenzenesulphonamido)-ethyl]-cinnamate
from ethyl 4-(2-aminoethyl)-cinnamate hydrochloride and 4-chlorobenzenesulphochloride; m.p. 97°–98° C. (recrystallized from ethanol); yield 92% of theory and therefrom by hydrolysis 4-[2-(4-chlorobenzenesulphonamido)-ethyl]-cinnamic acid; m.p. 173°–175° C.; yield 93% of theory.

(j) ethyl 4-[2-(1-naphthylsulphonamido)-ethyl]-cinnamate from ethyl 4-(2-aminoethyl)-cinnamate hydrochloride and 1-napthylsulphochloride; m.p. 85°–86° C. (recrystallized from ethanol); yield 88% of theory, and therefrom by hydrolysis 4-[2-(1-naphthylsulphonamido)-ethyl]-cinnamic acid m.p. 175° C. (recrystallized from ethanol+water); yield 93% of theory.

(k) ethyl 4-[2-(2-phenylethenesulphonamido)-ethyl]-cinnamate
from ethyl 4-(2-aminoethyl)-cinnamate hydrochloride and 2-phenylethenesulphochloride; m.p. 102°–104° C.; yield 63% of theory,
and therefrom by hydrolysis 4-[2-(2-phenylethenesulphonamido)-ethyl]-cinnamic acid; m.p. 190°–191° C.; yield 94% of theory.

(l) ethyl 4-{2-[2-(4-chlorophenyl)-ethenesulphonamido]-ethyl}-cinnamate
from ethyl 4-(2-aminoethyl)-cinnamate hydrochloride and 2-(4-chlorophenyl)-ethenesulphochloride; m.p. 131°–132° C. (recrystallized from ethanol); yield 83% of theory, and therefrom by hydrolysis 4-{2-[2-(4-chlorophenyl)-ethenesulphonamido]-ethyl}-cinnamic acid; m.p. 211°–212° C. (recrystallized from ethanol+water); yield 78% of theory.

EXAMPLE 3

4-[2-(4-Toluenesulphonamido)-ethyl]-phenylacetic acid

To a solution of 14.6 g. (60 mmol) ethyl 4-(2-aminoethyl)-phenylacetate hydrochloride in 120 ml. anhydrous pyridine, there is added dropwise at 0°–10° C. within the course of 5 minutes, a mixture of 12.0 g. (63 mmol) 4-toluenesulphochloride and 50 ml. pyridine, whereafter the reaction mixture is allowed to warm up to ambient temperature and then kept for 45 minutes at 60° C. The reaction mixture is subsequently evaporated in a vacuum to half its volume, poured into ice water and acidified with hydrochloric acid. The precipitated viscous mass is taken up in ethyl acetate and the solution is dried with anhydrous sodium sulphate and evaporated in a vacuum. The residue is recrystallized from a mixture of ethyl acetate and ligroin to give 18.0 g. (82% of theory) ethyl 4-[2-(4-toluenesulphonamido)-ethyl]-phenylacetate; m.p. 113°–115° C.

To a solution of 13.3 g. (37 mmol) ethyl 4-[2-(4-toluenesulphonamido)-ethyl]-phenylacetate in 220 ml. ethanol are added dropwise 110 ml. 1 N aqueous potassium hydroxide solution and the reaction mixture subsequently kept for 2 hours at 35°–40° C. The ethanol is then distilled off in a vacuum and the aqueous phase extracted with diethyl ether. The addition of 55 ml. 2 N hydrochloric acid leads to the separating out of a colorless precipitate which is filtered off with suction and recrystallized from a mixture of ethyl acetate and ligroin to give 10.8 g. (88% of theory) 4-[2-(4-toluenesulphonamido)-ethyl]-phenylacetic acid; m.p. 141°–143° C.

The following compounds are obtained in an analogous manner:

(a) ethyl 4-[2-(2-phenylethenesulphonamido)-ethyl]-benzoate
from ethyl 4-(2-aminoethyl)-benzoate hydrochloride and 2-phenylethenesulphochloride; m.p. 59°–61° C. (recrystallized from ethanol+water); yield 66% of theory,
and therefrom by hydrolysis 4-[2-(2-phenylethenesulphonamido)-ethyl]-benzoic acid; m.p. 169.5°–170° C. (recrystallized from ethyl acetate); yield 81% of theory.

(b) ethyl 4-[2-(2-phenylethanesulphonamido)-ethyl]-phenylacetate
from ethyl 4-(2-aminoethyl)-phenylacetate hydrochloride and 2-phenylethanesulphochloride colorless oil; yield 61% of theory, and therefrom by hydrolysis 4-[2-(2-phenylethanesulphonamido)-ethyl]-phenylacetic acid; m.p. 150°–152° C. (recrystallized from ethyl acetate); yield 69% of theory.

(c) ethyl 4-[2-(2-phenylethenesulphonamido)-ethyl]-phenylacetate
from ethyl 4-(2-aminoethyl)-phenylacetate hydrochloride and 2-phenylethenesulphochloride colorless oil; yield 78% of theory, and therefrom by hydrolysis 4-[2-(2-phenylethenesulphonamido)-ethyl]-phenylacetic acid; m.p. 146°–149° C. (recrystallized from ethyl acetate+ligroin); yield 81% of theory.

(d) ethyl 3-{4-[2-(2-chlorobenzenesulphonamido)-ethyl]-phenyl}-propionate
from ethyl 3-[4-(2-aminoethyl)-phenyl]-propionate hydrochloride and 2-chlorobenzenesulphochloride m.p. 57°–60° C.; yield 94% of theory, and therefrom by hydrolysis 3-{4-[2-(2-chlorobenzenesulphonamido)-ethyl]-phenyl}-propionic acid; m.p. 136°–139° C. (recrystallized from ethyl acetate+ligroin); yield 82% of theory.

(e) ethyl 3-{4-[2-(3-methoxybenzenesulphonamido)-ethyl]-phenyl}-propionate
from ethyl 3-[4-(2-aminoethyl)-phenyl]-propionate hydrochloride and 3-methoxybenzenesulphochloride colorless oil; yield 92% of theory, and therefrom by hydrolysis 3-{4-[2-(3-methoxybenzenesulphonamido)-ethyl]-phenyl}-propionic acid; m.p. 100°–103° C. (triturated with diethylether); yield 65% of theory.

(f) ethyl 3-{4-[2-(3-trifluoromethylbenzenesulphonamido)-ethyl]-phenyl}-propionate
from ethyl 3-[4-(2-aminoethyl)-phenyl]-propionate hydrochloride and 3-trifluoromethylbenzenesulphochloride colorless oil; yield 99% of theory, and therefrom by hydrolysis 3-{4-[2-(3-trifluoromethylbenzenesulphonamido)-ethyl]-phenoxy}-propionic acid; m.p. 119°–121° C. (recrystallized from toluene); yield 74% of theory.

(g) ethyl 3-<4-{2-[2-(4-chlorophenyl)-ethenesulphonamido]-ethyl}-phenyl>-propionate
from ethyl 3-[4-(2-aminoethyl)-phenyl]-propionate hydrochloride and 2-(4-chlorophenyl)-ethenesulphonyl chloride; m.p. 94°–96° C. (recrystallized from ethyl acetate+ligroin); yield 86% of theory, and therefrom by hydrolysis 3-<4-{2-[2-(4-chlorophenyl)-ethenesulphonamido]-ethyl}-phenyl>-propionic acid; m.p. 165° C. (recrystallized from ethyl acetate+methanol); yield 73% of theory.

EXAMPLE 4

4-[2-(4-Fluorobenzenesulphonamido)-ethyl]-phenylacetic acid

A mixture of 11.0 g. (51 mmol) 4-(2-aminoethyl)-phenylacetic acid hydrochloride, 8.3 g. (60 mmol) potassium carbonate and 200 ml. water is heated to 80° C. and, at this temperature, 9.5 g. (49 mmol) 4-fluorobenzenesulphochloride are added thereto. Thereafter, the reaction mixture is kept for a further 2 hours at 80° C., then cooled and brought to pH 2 by means of 2 N hydrochloric acid. The precipitate obtained is filtered off with suction, dried and recrystallized from 66% ethanol to give 10.2 g. (62% of theory) 4-[2-(4-fluorobenzenesulphonamido)-ethyl]-phenylacetic acid; m.p. 121°–122° C.

The following compounds are obtained in an analogous manner:

(a) 3-[4-(2-benzenesulphonamidoethyl)-phenyl]-propionic acid
from 3-[4-(2-aminoethyl)-phenyl]-propionic acid hydrochloride and benzenesulphochloride; m.p. 102.5°–103° C. (recrystallized from ethyl acetate+ligroin); yield 63% of theory (b) 4-(2-benzenesulphonamidoethyl)-benzoic acid from 4-(2-aminoethyl)-benzoic acid hydrochloride and benzenesulphochloride; m.p. 144.5°–145° C. (recrystallized from aqueous ethanol); yield 74% of theory.

(c) 4-[2-(4-methoxybenzenesulphonamido)-ethyl]-benzoic acid
from 4-(2-aminoethyl)-benzoic acid hydrochloride and 4-methoxybenzenesulphochloride; m.p. 177°–178° C. (recrystallized from aqueous ethanol); yield 68% of theory.

(d) 4-(2-benzenesulphonamidoethyl)-phenylacetic acid
from 4-(2-aminoethyl)-phenylacetic acid hydrochloride and benzenesulphochloride; m.p. 127°–128° C. (recrystallized from ligron+isopropanol); yield 92% of theory.

(e) 4-[2-(4-methoxybenzenesulphonamido)-ethyl]-phenylacetic acid
from 4-(2-aminoethyl)-phenylacetic acid hydrochloride and 4-methoxybenzenesulphochloride; m.p. 160°–162° C. (recrystallized from aqueous ethanol); yield 72% of theory.

(f) 4-[2-(4-acetylbenzenesulphonamido)-ethyl]-phenylacetic acid
from 4-(2-aminoethyl)-phenylacetic acid hydrochloride and 4-acetylbenzenesulphochloride; m.p. 193°–194° C. (recrystallized from aqueous ethanol); yield 82% of theory.

(g) 4-[2-(2-naphthalenesulphonamido)-ethyl]-phenylacetic acid
from 4-(2-aminoethyl)-phenylacetic acid hydrochloride and 2-naphthalenesulphochloride; m.p. 135°–136° C. (recrystallized from aqueous ethanol); yield 68% of theory.

(h) 4-(2-benzenesulphonamidoethyl)-cinnamic acid from 4-(2-aminoethyl)-cinnamic acid hydrochloride and benzenesulphochloride; m.p. 164°–166° C. (recrystallized from aqueous ethanol); yield 73% of theory.

(i) 4-(3-benzenesulphonamidopropyl)-benzoic acid from 4-(3-aminopropyl)-benzoic acid hydrochloride and benzenesulphochloride; m.p. 207.5°–209° C. (recrystallized from acetone+water); yield 63% of theory.

(j) 4-(benzenesulphonamidomethyl)-phenylacetic acid from 4-aminomethylphenylacetic acid hydrochloride and benzenesulphochloride; m.p. 144.5°–145.5° C. (recrystallized from ethyl acetate); yield 76% of theory.

(k) 4-(3-benzenesulphonamidopropyl)-phenylacetic acid from 4-(3-aminopropyl)-phenylacetic acid hydrochloride and benzenesulphochloride; m.p. 128°–129° C. (recrystallized from ethyl acetate+ligroin); yield 84% of theory.

(l) 2-[4-(2-benzenesulphonamidoethyl)-phenyl]-2-methylpropionic acid
from 2-[4-(2-aminoethyl)-phenyl]-2-methylpropionic acid hydrochloride and benzenesulphochloride; m.p. 86°–88° C. (recrystallized from ethyl acetate); yield 80% of theory.

(m) 3-{4-[2-(2,5-dichlorobenzenesulphonamido)-ethyl]-phenyl}-propionic acid
from 3-[4-(2-aminoethyl)-phenyl]acetic acid hydrochloride and 2,5-dichlorobenzenesulphochloride; m.p. 163°–164° C. (recrystallized from aqueous ethanol): yield 65% of theory.

(n) 4-[4-(2-benzenesulphonamidoethyl)-phenyl]-butyric acid
from 4-[4-(2-aminoethyl)-phenyl]-butyric acid hydrochloride and benzenesulphochloride; m.p. 70°–71° C. (recrystallized from aqueous ethanol); yield 67% of theory.

(o) 2-[4-(2-benzenesulphonamidoethyl)-phenyl]-propionic acid
from 2-[4-(2-aminoethyl)-phenyl]-propionic acid hydrochloride and benzenesulphochloride; m.p. (sodium salt) 236°–239° C.; yield 83% of theory.

(p) 3-[4-(2-benzenesulphonamidoethyl)-phenyl]-2-methylpropionic acid
from 3-[4-(2-aminoethyl)-phenyl]-2-methylpropionic acid hydrochloride and benzenesulphochloride; m.p. 113°–115° C. (recrystallized from ethyl acetate+ligroin); yield 85% of theory.

(q) 4-(2-benzenesulphonamidoethyl)-α-methylcinnamic acid from 4-(2-aminoethyl)-α-methylcinnamic acid hydrochloride and benzenesulphochloride; m.p. 147°–148° C. yield 62% of theory.

(r) 4-[2-(2-naphthylsulphonamido)-ethyl]-cinnamic acid from 4-(2-aminoethyl)-cinnamic acid hydrochloride and 2-naphthylsulphochloride; m.p. 192°–193° C. (recrystallized from ethanol+water); yield 96% of theory.

EXAMPLE 5

4-[2-(n-Hexadecanesulphonamido)-ethyl]-benzoic acid

To a mixture of 11.5 g. (50 mmol) ethyl 4-(2-aminoethyl)-benzoate hydrochloride, 150 ml. benzene and 20 g. (200 mmol) triethylamine there is added dropwise at 0° C., with vigorous stirring, 16.3 g. (50 mmol) n-hexadecanesulphonyl chloride. The reaction mixture is further stirred for 2 hours in an ice bath and then left to stand overnight at 20° C. It is then poured on to ice; rendered acidic with hydrochloric acid and extracted with diethyl ether. The ether phase is washed with water, dried with anhydrous sodium sulphate and evaporated. The residue is recrystallized from aqueous ethanol to give 17.0 g. (69% of theory) ethyl 4-[2-(n-hexadecanesulphonamido)-ethyl]-phenylacetate; m.p. 82°–83° C. (recrystallized from aqueous ethanol).

The ester is hydrolyzed, analogously to Example 1, with aqueous potassium hydroxide solution in methanol. Yield 86% of theory 4-[2-(n-hexadecanesulphonamido)-ethyl]-benzoic acid; m.p. 168°–169° C. (recrystallized from aqueous ethanol).

EXAMPLE 6

4-[2-(n-Octanesulphonamido)-ethyl]-phenylacetic acid 9.9 g. (43 mmol) Ethyl 4-(2-aminoethyl)-phenylacetate hydrochloride and 9.2 g. (43 mmol) n-octanesulphonyl chloride are suspended in 175 ml. benzene and a solution of 11.9 g. (86 mmol) potassium carbonate in 400 ml. water is added dropwise, with vigorous stirring, followed by stirring for 10 minutes, whereafter the phases are separated. The benzene phase is washed with water, dried with anhydrous sodium sulphate and evaporated in a vacuum. After recrystallization from aqueous ethanol, there are obtained 12.6 g. (79% of theory) ethyl 4-[2-(n-octanesulphonamido)-ethyl]-phenylacetate; m.p. 59°–60° C. (recrystallized from aqueous ethanol).

A mixture of 10.7 g. (29 mmol) of this ethyl ester, 29 ml. 2 N aqueous potassium hydroxide solution and 29 ml. ethanol is kept for 3 hours at 40° C., followed by distilling off the ethanol in a vacuum and acidification with hydrochloric acid. The precipitate is filtered off with suction and recrystallized from aqueous ethanol to give 9.0 g. (91% of theory) 4-[2-(n-octanesulphonamido)-ethyl]-phenylacetic acid; m.p. 156°–157° C.

The following compounds are obtained in an analogous manner:

ethyl 3-[4-(2-n-octylsulphonamidoethyl)-phenyl]-propionate from ethyl 3-[4-(2-aminoethyl)-phenyl]-propionate hydrochloride and n-octanesulphonyl chloride; m.p. 66°–68° C. (recrystallized from ethyl acetate+ligroin): yield 68% of theory, and therefrom by hydrolysis 3-[4-(2-n-octylsulphonamidoethyl)-phenyl]-propionic acid m.p. 146°–148° C. (recrystallized from ethyl acetate); yield 83% of theory.

EXAMPLE 7

4-(N-Methylbenzenesulphonamidomethyl)-cinnamic acid

A mixture of 5.1 g. (30 mmol) N-methylbenzenesulphonamide, 8.8 g. (33 mmol) ethyl 4-bromomethyl-cinnamate (m.p. 47° C.), 4.1 g. (30 mmol) potassium carbonate and 50 ml. dimethylformamide are heated, with stirring, for 4 days at 60° C. The reaction mixture is then cooled and stirred into cold water and the organic components extracted with diethyl ether. The ethereal solution is washed with 0.5 N aqueous sodium hydroxide solution, dried with anhydrous sodium sulphate and evaporated. The residue is recrystallized from isopropanol to give 7.9 g. (73% of theory) ethyl 4-(N-methylbenzenesulphonamidomethyl)-cinnamate; m.p. 112°–112.5° C.

From this, there is obtained, by hydrolysis with 1 N aqueous potassium hydroxide solution in methanol, 4-(N-methylbenzenesulphonamidomethyl)-cinnamic acid; m.p. 212°–214° C. (recrystallized from isopropanol+water); yield 89% of theory.

EXAMPLE 8

4-[2-(N-Methylbenzenesulphonamido)-ethyl]-phenylacetic acid

To a mixture of 10.4 g. (30 mmol) ethyl 4-(2-benzenesulphonamidoethyl)-phenylacetate (prepared by esterification of the acid according to Example 4 d with ethanol; m.p. 58°–60° C.), 60 ml. hexamethylphosphoric acid triamide and 60 ml. anhydrous toluene is added 0.72 g. (30 mmol) sodium hydride (as a mineral oil suspension) and the reaction mixture subsequently stirred for 2 hours at 80° C. It is then cooled, mixed with a mixture of 12.8 g. (90 mmol) methyl iodide and 12 ml. hexamethylphosphoric acid triamide, stirred for 15 minutes at 20° C. and then kept for 3 hours at 80° C. After cooling, the reaction mixture is poured on to ice, brought to pH 3 with hydrochloric acid and extracted several times with toluene. The toluene phase is evaporated and the evaporation residue chromatographed with silica gel/toluene to give 5.1 g. (47% of theory) pure ethyl 4-[2-(N-methylbenzenesulphonamido)-ethyl]-phenylacetate in the form of a colorless oil with the refractive index $n_D^{20} = 1.5590$.

From this is obtained, by hydrolysis with 1 N aqueous potassium hydroxide solution: 4-[2-(N-methylbenzenesulphonamido)-ethyl]-phenylacetic acid; m.p. 159°–160° C. (recrystallized from ethyl acetate); yield 63% of theory.

EXAMPLE 9

4-(2-Benzenesulphonamidoethyl)-phenylacetic acid

To an ice-cooled mixture of 52.3 g. (0.2 mol) N-(2-phenylethyl)-benzenesulphonamide, 80 ml. 1,1,2,2-tetrachloroethane and 40.8 g. (0.52 mol) acetyl chloride are added portionwise, with stirring, 88 g. (0.664 mol) aluminium trichloride. The addition is ended after 1.5 hours. The reaction mixture is left for a further 45 minutes at 0° C. and then gradually heated to 80° C. After 1.5 hours, it is poured on to ice and the organic phase is separated off. The aqueous portion is extracted with methylene chloride and the combined organic phases are dried with anhydrous sodium sulphate and evaporated. The residue is heated to reflux temperature, with stirring, for 2 hours with 1 liter 2 N aqueous sodium hydroxide solution. After cooling, the reaction mixture is extracted with methylene chloride and the organic phase is dried with anhydrous sodium sulphate and evaporated. The residue is triturated with diethyl ether and the crystals obtained are filtered off with suction to give 31.3 g. (52% of theory) 4-(2-benzenesulphonamidoethyl)-acetophenone; m.p. 133°–135° C.

A mixture of 9.4 g. (31 mmol) 4-(2-benzenesulphonamidoethyl)-acetophenone, 1.6 g. (50 mmol) sulphur and 20 ml. morpholine are heated, with stirring, for 19 hours at 135° C. After cooling, the reaction mixture is poured into water and the aqueous phase is extracted with methylene chloride. The methylene chloride phase is washed with 1 N hydrochloric acid, dried with anhydrous sodium sulphate and evaporated. The evaporation residue is taken up in 100 ml. 1 N aqueous sodium hydroxide solution and the solution is boiled for 2 hours. After cooling, the reaction mixture is extracted with ethyl acetate and, by the addition of hydrochloric acid, 4-(2-benzenesulphonamidoethyl)-phenylacetic acid, which, in all its physical properties, is identical with the product of Example 4 d, is precipitated from the aqueous phase; yield 56% of theory.

EXAMPLE 10

4-(2-Benzenesulphonamidoethyl)-benzoic acid 11.0 g. (0.28 mol) sodium hydroxide are dissolved in 90 ml. water, 66 ml. dioxan are added thereto and the reaction mixture is mixed dropwise, while stirring, with 16 g. (0.1 mol) bromine. The reaction mixture is cooled in an ice bath, with further stirring, and 10 g. (0.033 mol) 4-(2-benzenesulphonamidoethyl)-acetophenone are added thereto. After 2 hours, the desired carboxylic acid is precipitated by the addition of hydrochloric acid. It is recrystallized from aqueous ethanol to give 8.2 g. (81% of theory) 4-(2-benzenesulphonamidoethyl)-benzoic acid which, in all its physical properties, is identical with the product of Example 4 b.

EXAMPLE 11 n-Butyl 4-(benzenesulphonamidomethyl)-phenylacetate

A mixture of 6.11 g. (20 mmol) 4-(benzenesulphonamidomethyl)-phenylacetic acid (see Example 4 j), 2.83 g. (20 mmol) boron trifluoride etherate and 40 ml. n-butanol is heated, while stirring, for 3 hours at reflux temperature, whereafter the greater part of the excess n-butanol is evaporated off in a vacuum and the residue is diluted with 100 ml. ice water. The mixture is extracted with diethyl ether and the combined extracts are successively washed with 2 N hydrochloric acid, water and aqueous sodium hydrogen carbonate solution, dried with anhydrous sodium sulphate and evaporated. The residue is recrystallized from a mixture of diethyl ether and ligroin to give 6.1 g. (84% of theory) n-butyl 4-(benzenesulphonamidomethyl)-phenylacetate; m.p. 60.5°–61° C.

EXAMPLE 12

4-(2-Benzenesulphonamidoethyl)-phenylacetic acid [4-methylpiperazide]

A mixture of 16.0 g. (0.05 mol) 4-(2-benzenesulphonamidoethyl)-phenylacetic acid, 100 ml. benzene and 17.9 g. (0.15 mol) thionyl chloride is heated for 5 hours at reflux temperature. Benzene and excess thionyl chloride are then distilled off in a vacuum, the yield of crude product being quantitative. After recrystallization from toluene, there are obtained 14.9 g. (88% of theory) 4-(2-benzenesulphonamidoethyl)-phenylacetyl chloride; m.p. 82° C. (decomp.).

To an ice-cooled solution of 3.0 g. (30 mmol) N-methylpiperazine and 100 ml. anhydrous pyridine are added portionwise, with stirring, in the course of one hour, 10.1 g. (30 mmol) 4-(2-benzenesulphonamidoethyl)-phenylacetyl chloride. Subsequently, the reaction mixture is allowed to warm up to 20° C., then heated for 5 hours at 90° C., cooled and poured into about 500 ml. ice water. The mixture is extracted with methylene chloride and the methylene chloride phase, after drying with anhydrous sodium sulphate, is evaporated. The residue is taken up in diethyl ether and the hydrochloride precipitated with ethereal hydrochloric acid. After recrystallization from ethanol, there are obtained 8.7 g. (66% of theory) 4-(2-benzenesulphonamidoethyl)-phenylacetic acid [4-methylpiperazide]hydrochloride; m.p. 168° C.

EXAMPLE 13

Tablets are prepared, each of which contains 10 mg. 3-[4-(2-benzenesulphonamidoethyl)-phenyl]-propionic acid. The tablets are produced according to the following formulation:

| | |
|---|---|
| 3-[4-(2-benzenesulphonamidoethyl)-phenyl]-propionic acid | 10 g. |
| lactose | 80 g. |
| starch | 29 g. |
| magnesium stearate | 1 g. |

The propionic acid derivative is finely pulverised and mixed with the lactose and starch. The mixture is granulated in conventional manner. The magnesium stearate is added to the granulate and the mixture is pressed to give 1000 tablets, each having a weight of 0.12 g.

It will be understood that the specification and examples are illustrative but not limitative of the present invention and that other embodiments within the spirit and scope of the invention will suggest themselves to those skilled in the art.

What is claimed is:

1. Sulphonamide compound of the formula

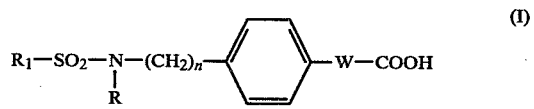

(I)

wherein
R is hydrogen or lower alkyl;
$R_1$ is alkyl of up to 16 carbon atoms except when R is H, aryl having 6 to 14 carbon atoms, aralkyl with an alkyl moiety of up to 5 carbon atoms or aralkenyl with an alkenyl moiety of 2 or 3 carbon atoms, the aryl moiety of which in either case having 6 to 14 carbon atoms and being optionally substituted with one or more hydroxyl, fluorine, chlorine, bromine, trifluoromethyl, lower alkyl or alkoxy or by acetyl, carboxy or alkoxycarbonyl with 1–5 carbon atoms in the alkoxy moiety, radical;
n is 1, 2 or 3; and
W is a valence bond or a divalent aliphatic hydrocarbon linkage having up to 6 carbon atoms; and
the physiologically acceptable salt, lower alkyl ester or amide of the WCOOH group of such compound wherein the amide component is selected from the group consisting of ammonia, p-aminobenzoic acid, beta-alanine; ethanolamine, 2-aminopropanol, alkylamine, dialkylamine, 4-alkylpiperazine, 4-aralkylpiperazine and 4-arylpiperazine.

2. Compound as claimed in claim 1 wherein R is hydrogen.

3. Compound as claimed in claim 1 wherein R is lower alkyl of up to 5 carbon atoms.

4. Compound as claimed in claim 1 wherein $R_1$ is alkyl of up to 16 carbon atoms.

5. Compound as claimed in claim 1 wherein $R_1$ is aryl of from 6 to 14 carbon atoms.

6. Compound as claimed in claim 1 wherein $R_1$ is substituted aryl of from 6 to 14 carbon atoms, the substituent being selected from hydroxyl, halogen, alkyl, alkoxy, trifluoromethyl, carboxyl and acyl.

7. Compound as claimed in claim 1 wherein $R_1$ is aralkyl with up to 5 carbon atoms in the alkyl moiety.

8. Compound as claimed in claim 1 wherein $R_1$ is substituted aralkyl with up to 5 carbon atoms in the alkyl moiety wherein the aryl moiety is substituted by at least one of hydroxyl, fluorine, chlorine, bromine, trifluoromethyl, lower alkyl, lower alkoxy, acetyl, carboxy or alkoxycarbonyl with 1–5 carbon atoms in the alkoxy moiety, radical.

9. Compound as claimed in claim 1 wherein $R_1$ is aralkenyl with from 2 or 3 carbon atoms in the alkenyl moiety.

10. Compound as claimed in claim 1 wherein $R_1$ is substituted aralkenyl with from 2 or 3 carbon atoms in the alkenyl moiety wherein the aryl moiety is sibstituted by at least one of hydroxyl, fluorine, chlorine, bromine, trifluoromethyl, lower alkyl, lower alkoxy, acetyl, carboxy or alkoxycarbonyl with 1–5 carbon atoms in the alkoxy moiety, radical.

11. Compound as claimed in claim 1 wherein n is 1.
12. Compound as claimed in claim 1 wherein n is 2.
13. Compound as claimed in claim 1 wherein n is 3.
14. Compound as claimed in claim 1 wherein W is a valence bond.
15. Compound as claimed in claim 1 wherein W is a saturated divalent aliphatic hydrocarbon linkage.
16. Compound as claimed in claim 1 wherein W is alkenylene.
17. Compound as claimed in claim 1 wherein W is alkylene or alkenylene of up to 5 carbon atoms.
18. Compound as claimed in claim 1 wherein W is $CH_2$.
19. Compound as claimed in claim 1 wherein W is $CH_2CH_2$.
20. Compound as claimed in claim 1 wherein W is $—C(CH_3)_2—$.
21. Compound as claimed in claim 1 wherein $R_1$ is phenyl.
22. Compound as claimed in claim 1 wherein $R_1$ is phenyl substituted by 1 or 2 chlorine, fluorine, methoxy or trifluoromethyl groups.
23. Compound as claimed in claim 1 wherein W is alkylene of up to 3 carbon atoms and R is hydrogen.
24. Compound as claimed in claim 1 designated 4-[2-(4-toluenesulphoamido)-ethyl]-phenylacetic acid.
25. Compound as claimed in claim 1 designated 3-[4-(2-benzenesulphonamidoethyl)-phenyl]-propionic acid.
26. Compound as claimed in claim 1 designated 4-(2-benzenesulphonamidoethyl)-phenylacetic acid.
27. Compound as claimed in claim 1 designated 4-(3-benzenesulphonamidopropyl)-phenylacetic acid.
28. Compound as claimed in claim 1 designated 3-{4-[2-(2,5-dichlorobenzenesulphonamido)-ethyl]-phenyl}-propionic acid.
29. Method for inhibiting thrombocyte aggregation in an afflicted host, which method comprises administering to such host effective amounts of a sulphonamide compound of the formula

(I)

wherein
R is hydrogen or lower alkyl;
$R_1$ is alkyl of up to 16 carbon atoms, aryl of 6 to 14 carbon atoms, aralkyl with an alkyl moiety of up to 5 carbon atoms or aralkenyl with an alkenyl moiety of 2 to 3 carbon atoms the aryl moiety of which in either case having 6 to 14 carbon atoms and being optionally substituted with one or more hydroxyl, fluorine, chlorine, bromine, trifluoromethyl, lower alkyl or alkoxy or by acetyl, carboxy or alkoxycarbonyl with 1 to 5 atoms in the alkoxy moiety, radical;
n is 1, 2 or 3; and
W is a valence bond or a divalent aliphatic hydrocarbon linkage, and
the physiologically acceptable salt, lower alkyl ester or amide of the WCOOH group of such compound wherein the amide component is selected from the group consisting of ammonia, p-aminobenzoic acid, beta-alanine; ethanolamine, 2-aminopropanol, alkylamine, dialkylamine, 4-alkylpiperazine, 4-aralkylpiperazine and 4-arylpiperazine.

30. Method as claimed in claim 29 wherein said sulphonamide compound is selected from
4-[2-(4-toluenesulphoamido)-ethylphenylacetic acid;
3-[4-(2-benzenesulphonamidoethyl)-phenyl]-propionic acid;
4-(2-benzenesulphonamidoethyl)-phenylacetic acid;
4-(3-benzenesulphonamidopropyl)-phenylacetic acid; and
3-{4-[2-(2,5-dichlorobenzenesulphonamido)-ethyl]-phenyl}-propionic acid.

31. Composition for depressing lipids, and inhibiting thrombocyte aggregation, which composition comprises a pharmacologically acceptable carrier and, in effective amounts, a sulphonamide compound of the formula

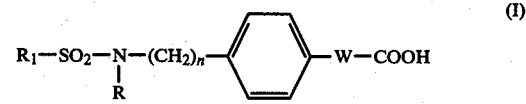

(I)

wherein
R is hydrogen or lower alkyl;
$R_1$ is alkyl of up to 16 carbon atoms, aryl of 6 to 14 carbon atoms or aralkenyl with an alkenyl moiety of 2 to 3 carbon atoms the aryl moiety of which in either case having 6 to 14 carbon atoms and being optionally substituted with one or more hydroxyl, fluorine, chlorine, bromine, trifluoromethyl, lower alkyl or alkoxy or by acetyl lower alkanyl, carboxy or alkoxycarbonyl with 1 to 5 carbon atoms in the alkoxy moiety, radical;
n is 1, 2 or 3; and
W is a valence bond or a divalent aliphatic hydrocarbon linkage, and
the physiologically acceptable salt, lower alkyl ester or amide of the WCOOH group of such compound wherein the amide component is selected from the group consisting of ammonia, p-aminobenzoic acid, beta-alanine; ethanolamine, 2-aminopropanol, alkylamine, dialkylamine, 4-alkylpiperazine, 4-aralkylpiperazine and 4-arylpiperazine.

32. Method for depressing lipids in an afflicted host, which method comprises administering to such host effective amounts of a sulphonamide compound of the formula

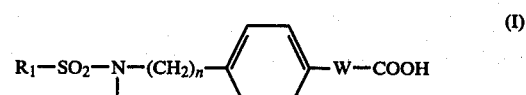

(I)

wherein
R is hydrogen or lower alkyl;

$R_1$ is alkyl of up to 16 carbon atoms, aryl of 6 to 14 carbon atoms or aralkenyl with an alkenyl moiety of 2 to 3 carbon atoms the aryl moiety of which in either case having 6 to 14 carbon atoms and being optionally substituted with one or more hydroxyl, fluorine, chlorine, bromine, trifluoromethyl, lower alkyl or alkoxy or by acetyl lower alkanyl, carboxy or alkoxycarbonyl with 1 to 5 carbon atoms in the alkoxy moiety, radical;

n is 1, 2 or 3; and

W is a valence bond or a divalent aliphatic hydrocarbon linkage, and the physiologically acceptable salt, lower alkyl ester or amide of the WCOOH group of such compound wherein the amide component is selected from the group consisting of ammonia, p-aminobenzoic acid, beta-alanine; ethanolamine, 2-aminopropanol, alkylamine, dialkylamine, 4-alkylpiperazine, 4-aralkylpiperazine and 4-arylpiperazine.

33. Method as claimed in claim 32 wherein said sulphonamide compound is selected from 4-[2-(4-toluenesulphoamido)-ethyl]-phenylacetic acid;

3-[4-(2-benzenesulphonamidoethyl)-phenyl]-propionic acid;

4-(2-benzenesulphonamidoethyl)-phenylacetic acid;

4-(3-benzenesulphonamidopropyl)-phenylacetic acid; and

3-{4-[2-(2,5-dichlorobenzenesulphonamido)-ethyl]-phenyl}-propionic acid.

* * * * *